United States Patent [19]
Salyer

[11] Patent Number: 5,116,165
[45] Date of Patent: May 26, 1992

[54] ACETABULAR REAMER CUP

[75] Inventor: Paul E. Salyer, Warsaw, Ind.

[73] Assignee: Othy, Inc., Warsaw, Ind.

[21] Appl. No.: 667,174

[22] Filed: Mar. 11, 1991

[51] Int. Cl.$^5$ ............................ A61B 17/16; B23C 5/12
[52] U.S. Cl. ........................................ 407/54; 407/61; 606/81
[58] Field of Search .................... 606/79–81, 606/85; 407/34, 58, 59, 61–63, 54

[56] References Cited

U.S. PATENT DOCUMENTS

| | | | |
|---|---|---|---|
| 2,785,673 | 3/1957 | Anderson | 606/81 X |
| 4,023,572 | 5/1977 | Weigand et al. | 606/81 |
| 4,116,200 | 9/1978 | Braun et al. | 606/81 |
| 4,131,116 | 12/1978 | Hedrick | 408/227 X |
| 4,811,632 | 3/1989 | Salyer | 76/115 |

Primary Examiner—Steven C. Bishop
Attorney, Agent, or Firm—Lundy & Associates

[57] ABSTRACT

An acetabular reamer cup having a cutting bowl having a plurality of singly curved cutting edges. The cutting bowl has a plurality of slots proceeding the cutting edges. The cutting bowl defines an axis of rotation. A bottom is joined to the cutting bowl. The bottom has a tool driver opening concentric with the axis of rotation.

20 Claims, 2 Drawing Sheets

ACETABULAR REAMER CUP

BACKGROUND OF THE INVENTION

The present invention pertains to acetabular reamers and more particularly pertains to an acetabular reamer cup.

Acetabular reamers are used by surgeons to prepare pelvis bones for insertion of artificial hip joints. An acetabular reamer is rotated to cut a cavity into the bone into which the socket portion of the artificial hip joint can be inserted. Dimensions and shape of the cavity cut are critical as the tolerances between the cavity and the socket portion of an artificial hip joint must be small to ensure proper function. This is especially true with the newly available "cementless" hip joints. Before "cementless" hip joints, the socket portion of the joint was cemented into the cavity in the pelvis bone. In the "cementless" joint, the socket portion is frictionally fit into the cavity, placing new importance upon accurate cavity dimensions and tolerances.

An acetabular reamer is composed of an acetabular reamer cup mounted on a tool driver, which in turn is mounted in the chuck or collet of a portable drill or flexible powered shaft. Acetabular reamer cups have a complex arrangement of precisely shaped cutting surfaces extending outward from an essentially hemispherical shell. Acetabular reamer cups are separable from their tool drivers for changing cup size prior to or during surgery, cleaning, and sharpening.

Acetabular reamers must be capable of producing cavities with very close tolerances and must also minimize any risk of causing contamination. Acetabular reamer cups have precise dimensions and are light in weight and must fit on an appropriate tool driver with a minimum of free play and must be quick and easy to install and remove without tools.

In the past, acetabular reamer cups have failed to provide a microscopically smooth surface with ideal tolerances for the implant. Acetabular reamer cups currently in use are characterized by generally rough, convex surfaces possessing a multitude of cutting edges. Unlike the present invention, the cutting edges are curved tangentially and result in an overall knobby surface. Thus, microscopically, upon rotation of the reamer cup, the knobby surface tends to grab and jump and chip resulting in a gouged and rough and uneven surface cavity whereby the accuracy of tolerances between the cavity and the implant ball that is gained by the precision in manufacture is thereby lost due to the undesirable cutting action and, in a large degree, the difficulty in operating and controlling precise cutting action of the knobby cup.

Some previous acetabular reamers have used an openbottom acetabular reamer cup gripped on the tool driver by means of a flange and slot and an opposed springloaded ball catch, like that on a socket wrench or socket driver. This presents a problem in that the catch tends to trap dried blood, which is very difficult to remove during cleaning. An additional problem is that unless tolerances of cups and tool drivers are made very close, at great cost, there is considerable free play between a cup and its tool driver. This increases wear and decreases the precision of the tool.

An alternative acetabular reamer, described in U.S. Pat. No. 4,811,632, utilizes a convex-bottomed acetabular reamer cup having a large central opening complementary in shape to a flange on the tool driver. Since the tool driver also grips the cup with a clamping action, extremely close tolerances are not required to prevent free play between the cup and driver. The convex bottom of the cup eliminates internal ninety degree angles, which could catch contaminants and the large central opening permits easy cleaning. The acetabular reamer cup is, however, complex in shape and expensive and, like all acetabular reamer cups, difficult to resharpen.

It is therefore highly desirable to provide an improved acetabular reamer cup.

It is also highly desirable to provide an improved acetabular reamer cup which fits on a tool driver with a minimum of free play.

It is also highly desirable to produce an acetabular reamer cup having a smooth cutting action.

It is also highly desirable to provide an improved acetabular reamer cup that has a controlled cutting action that will yield a surface cavity of more precise dimensions.

It is also highly desirable to provide an improved acetabular reamer cup that will produce a smooth surface with precise dimensions with less reliance on the operator's skill and ability to control the tool.

It is also highly desirable to provide an improved acetabular reamer cup which is precise in size, light in weight and inexpensive.

It is also highly desirable to provide an improved acetabular reamer cup which is quick and easy to install and remove from a tool driver without tools.

It is finally highly desirable to provide an improved acetabular reamer cup which meets all of the above desired features.

SUMMARY OF THE INVENTION

It is an object of the invention to provide an improved acetabular reamer cup.

It is another object of the invention to provide an improved acetabular reamer cup which fits on a tool driver with a minimum of free play.

It is another object of the invention to provide an acetabular reamer cup having a smooth cutting action.

It is another object of the invention to provide an improved acetabular reamer cup that has a controlled cutting action that will yield a surface cavity of more precise dimensions.

It is another object of the invention to provide an improved acetabular reamer cup that will produce a smooth surface with precise dimensions with less reliance on the operator's skill and ability to control the tool.

It is another object of the invention to provide an improved acetabular reamer cup which is precise in size, light in weight and inexpensive.

It is another object of the invention to provide an improved acetabular reamer cup which is quick and easy to install and remove from a tool driver without tools.

It is finally an object of the invention to provide an improved acetabular reamer cup which provides all of the above objects.

In the broader aspects of the invention there is provided an acetabular reamer cup having a cutting bowl having a plurality of singly curved cutting edges. The cutting bowl has a plurality of slots preceeding the cutting edges. The cutting bowl defines an axis of rotation. A bottom is joined to the cutting bowl. The bottom has a tool driver opening concentric with the axis of rotation.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
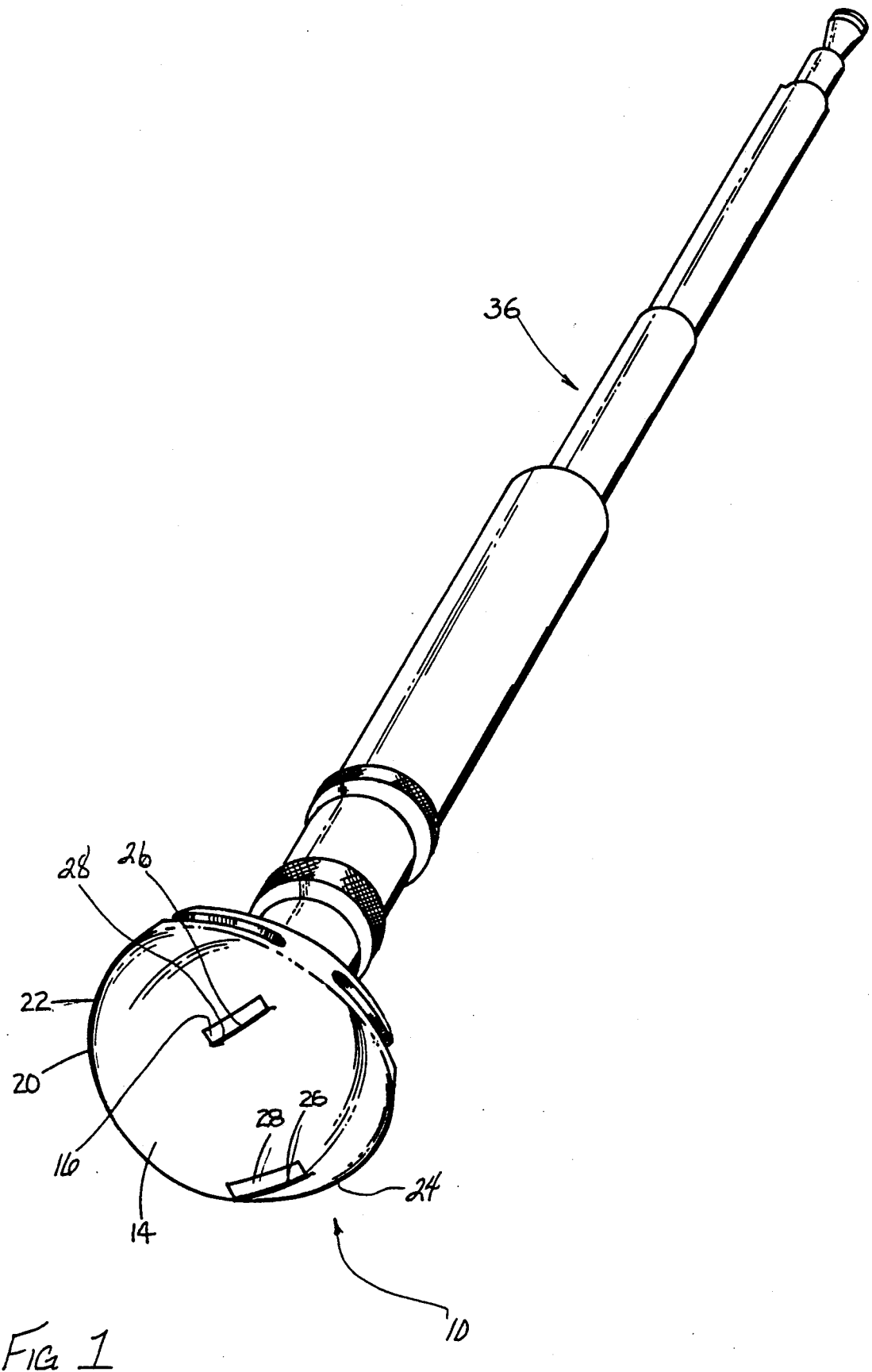
FIG. 1 is a perspective view of an embodiment of the acetabular reamer cup of the invention mounted on a tool driver.
Figure 2:
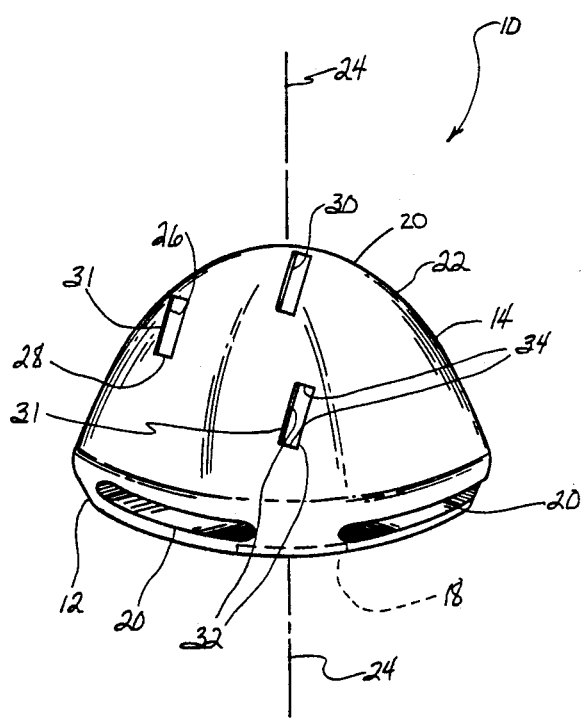
FIG. 2 is a semi-diagrammatical side plan view of the acetabular reamer cup of FIG. 1.
Figure 3:
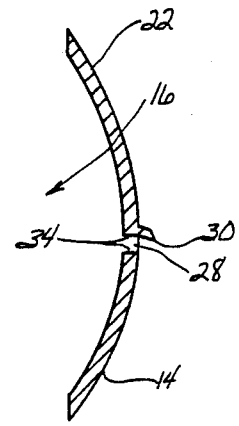
FIG. 3 is a partial cross-sectional view of the acetabular reamer cup of FIG. 1 taken substantially along line 3—3.

The acetabular reamer cup 10 of the invention has a bottom 12 and a cutting bowl 14, which together surround a hollow debris compartment 16. Bottom 12 may be flat or may be angled rearward, so as to eliminate internal ninety degree angles, which could retain contaminants. Bottom 12 has a tool driver opening 18, which is concentric with cutting bowl 14. Debris openings 20 may be provided for clearance of debris during use.

Cutting bowl 14 has a body portion 22 which is substantially hemispherical in shape and has an axis of rotation 24. Cutting bowl 14 has a spirally arranged pattern of outwardly extending cutters 26 and adjoining slots 28. Each acetabular reamer cup 10 has a particular handedness, that is, a direction of rotation about axis of rotation 24 in which acetabular reamer cup 10 must be rotated in order for acetabular reamer cup 10 to cut. Each slot 28 preceeds a respective cutter 26, that is, during rotation of the acetabular reamer cup 10 about axis of rotation 24, each slot 28 sweeps an area before a respective cutter 26. With a right handed acetabular reamer cup 10 that cuts when pressed against a substrate and rotated in a clockwise direction, slots 28 are to the right of respective cutters 26.

Each cutter 26 has a continuous cutting edge 30 or 31, which is disposed at a constant separation from and generally parallel to the hemispherical surface of body portion 22. Each cutting edge 30 or 31 is singly curved, that is, each cutting edge 30 or 31 is curved to be substantially parallel to the hemispherical surface of cutting bowl 14. Stated another way, each cutting edge 30 or 31 is parallel to a great circle: a straight line projected onto the hemisphere of the cutting bowl 14. In a particular embodiment of the invention, cutting edges 30 or 31 each have a longest dimension parallel to body portion 22 of cutting bowl 14 of about 0.500 inches. Longer cutting edges tend to cause chipping and result in uneven cut surfaces. Shorter cutting edges result in more of them as will be apparent from this disclosure.

Slots 28 similarly have substantially the shape of rectangles wrapped about the hemispherical surface of the cutting bowl 14. Slots 28 thus each have two pair of opposed margins: long margins 32 and short margins 34, each of which is singly curved. In a particular embodiment of the invention, long margins 34 each having a length about equal to five times the length of the short margins 32. In a particular embodiment, slots 28 are approximately about 0.500 inches by about 0.100 inches.

Slots 28 which are wider than about 0.100 inches tend to allow bone fragments to fall into the cavity of the bone requiring cleaning prior to inserting the socket of the hip joint. Also, extremely large slots tend to weaken bowl 14.

Cutting bowl 14 has a single lead cutting edge 30, which intersects the axis of rotation 24 and lies in a plane extending radial to axis of rotation 24. Extending rearwardly from lead cutting edge 30 in a spiral pattern are a series of follower cutting edges 31, each of which extends at an angle between about 12 degrees and about 20 degrees to a plane extending radial to axis of rotation 24. Greater than about 20 degrees, one end of cutting edges 30 and 31 drag. Less than about 12 degrees, cutting edges 30 and 31 chip bone rather than cut bone, thereby tending to produce an unevenly cut surface. Cutting edges 30 or 31 are arranged so that upon rotation of cutting bowl 14 about axis of rotation 24, each cutting edge 30 or 31 sweeps an area overlapped by one or more other cutting edges 30 or 31. In a particular embodiment of the invention, there are five follower cutting edges 31, each of which extends at an angle of about 17 degrees to a plane extending radially of axis of rotation 24 and each follower cutting edge 31 sweeps an area overlapped by other cutting edges 30 or 31, a total of about one and one-half times. In a particular embodiment of the invention, cutting edges 30 and 31 have a uniform length and have a single bevel opposite respective slots 28. In other particular embodiments, from about four to about nine cutting edges 30 and 31 are used on bowls 14 ranging from about 40 mm to about 80 mm in diameter.

Cutting edges 30 and 31 as above mentioned, are both singly curved and angularly disposed to a plane extending radially of the axis of rotation of the reamer cup 10. In a preferred embodiment, the curvature of cutting edges 30 and 31 are substantially the same as the curvature of the cutting bowl 14. Both the curvature and the angular disposition of the cutting edges 30 and 31 allow the cutting edges 30 and 31 to engage the bone being cut angularly in contrast to perpendicularly or "head on", thereby providing for a smooth cutting of the bone. It has been found that engaging bone "head on" or at right angles with a cutting edge may tend to result in chipping of the bone rather than cutting the bone. Thus, the curvature of cutting edges 30, 31 and their angular alignment to the axis of rotation provide that the cutting edges always cut the bone in "shear" and slide against the bone. This "shear" action of the cutting edges both prolongs the sharpness and therefore the usefulness of the cutting edge, and reduces chipping, thereby improving the tolerances which can be accomplished by the acetabular reamer cup 10 of the invention.

There are two preferred embodiments of the invention. The first preferred embodiment includes cutting edges 30 and 31 which extend at an angle between about 12 and about 20 degrees to a plane extending radial to the axis of rotation 24, but which have edges most distant from bottom 12 which trail as the acetabular reamer cup 10 is rotated. In the second preferred embodiment, cutting edges 30 and 31 which extend between about 12 to about 20 degrees to a plane extending radially of the axis of rotation 24 such that the edge most adjacent bottom 12 leads as the acetabular reamer cup 10 of the invention rotates. The acetabular reamer cup 10 of the invention above-disclosed allows for both an active or aggressive cutter and a passive cutter, as will be hereinafter described.

The acetabular reamer cup 10 of the invention may be manufactured generally in the same way as taught in U.S. Pat. No. 4,811,632 issued on Mar. 14, 1989, the specification of which is incorporated herein by reference. A bowl shaped cup blank is first fabricated by drawing or otherwise. In a particular embodiment, bowl 14 is made of 19 gauge (0.040″) 410 stainless steel material. The cup blank is then perforated with a plurality of holes, each surrounded by a margin. In the specific embodiment described herein, each of the holes is elongated. In the specific embodiment illustrated in the drawings, these holes are rectangular in shape. If the perforation of the cup blank produces burrs, the perforated cup blank must be deburred. The holes are cut in the blank angularly to a plane extending radially from the axis of rotation as above described. The cutting portion of the margin of each hole is subsequently deformed outwardly to yield a relieved cup blank and to result in a cutting portion which is curved generally in the direction of the surface of the cup blank. In the specific embodiment described herein, the cutting portions extend over the entire length of a respective margin. The margins extend from end to end of the perforation, and have the same dimension as the longitudinal dimension of the perforation. The outer surface of the relieved cup blank is then smoothed. Smoothing may be performed by sanding or grinding or any equivalent procedure. This removes a part of each of the cutting portions, sharpens the cutting portion, and forms a sharpened bevel. The cutting edges are subsequently raised from the cutting portions. In a specific embodiment of the invention, the height of the cutting edges from the outside surface of the cup is the same within a selected tolerance. In that embodiment, the tolerance is from about 0.015 to about 0.025 inches. After a cutting edge is raised, its bevel protrudes from the outer surface of the reamer cup. The cutting edges do not need additional sharpening before use.

Comparing the acetabular reamer cup 10 of the invention with prior acetabular reamers, a cavity can be formed in a pelvic bone with smaller tolerances than heretofore possible because of the greater consistency between cutting edges. With the acetabular reamer cup of the invention 10, plus or minus 0.010 inches tolerances can be achieved, whereas heretofore, normal tolerances were plus or minus 0.030 inches and the tolerances of the best acetabular reamer cups were plus or minus 0.020 inches. Minimal tolerances are desirable with the new "cementless" joints.

The acetabular reamer cup 10 of the invention is used in the same manner as other acetabular reamer cups by mounting the cup 10 on an appropriate tool driver 36. Acetabular reamer cup 10 of the invention is pressed against the pelvis of a patient while it is rotating and a cavity is cut for implantation of the artificial hip joint.

The active and passive acetabular reamer cups 10 of the invention allow a surgeon to choose reamer cups in accordance with the hardness of the bone the strength required to accomplish the cutting and other variables which are personal to the surgeon or patient. The active or aggressive cutter above described, upon rotation actually "digs in" to the bone as it cuts the bone. Because of the angular positioning of cutting edges 30 and 31, the active cutter of the invention has a tendency to burrow into the bone analogous to a screw being inserted into a block of wood.

In contrast, the passive acetabular reamer cup 10 of the invention cuts the bone by contact between the cutting edges 30 and 31 and the bone but does not "dig in" to the bone during the cutting operation. The passive acetabular reamer cup of the invention thus requires more force on the part of the surgeon to cut the bone than the active or aggressive acetabular reamer cup 10 of the invention. This gives the surgeon more "control" over the cutting operation. At all times during the cutting operation, the passive acetabular reamer cup of the invention always tends to extricate itself from the bone analogous to the screw above mentioned being rotated counterclockwise in a block of wood. The improved tolerances of the acetabular reamer cup 10 of the invention was documented by comparison testing. An embodiment of the acetabular reamer cup 10 of the invention having the following characteristics: 46 mm radius, 5 follower cutting edges, slot dimensions on the hemisphere of about 0.100 by 0.500 inches, a cutter height of about 0.020 inches, follower cutting edge angle of about 17 degrees, and cutting edge lengths of about 0.500 inches was compared to a 46 mm acetabular reamer cup manufactured in accordance with U.S. Pat. No. 4,811,632. The reamer cups of the patent and this invention were tested utilizing mahogany blocks approximately 2.75 inches square with a 0.5 inch pilot hole and a model 1034 milling and drilling machine as manufactured by Enco Manufacturing Company of Illinois. This milling machine is belted to operate at 300 rpm and equipped with a dial indicator having a travel from 0.001 inches to 1.00 inches, and a catalog no. 4000 electronic timer manufactured by the West Bend Company, West Bend, Wis.

Each acetabular reamer cup was placed on a selected tool driver 36. A new mahogany block was used for each test. The mahogany block was placed in a vise located at the base of the sharpness tester, and the vise was tightened until the mahogany block was firm in place. The tool driver with the acetabular reamer cup attached was lowered down onto the top of the block. The switch was turned on and the reamer cup was urged into the block.

The cavity cut into the block by the two acetabular reamer cups were measured by an inside caliper and a radius gauge. The test results are indicated in Table 1. As indicated in Table I, the acetabular reamer cup of the invention provides a controllable and smooth cutting action and yields a surface cavity of more precise dimensions.

TABLE I

| | Comparison/Inches | | | |
|---|---|---|---|---|
| | 1 | 2 | 3 | 4 |
| Acetabular Reamer Cup of the Invention | | | | |
| Diameter | 1.819 | 1.804 | 1.812 | 1.809 |
| Spherocity | 1.819/1.805 | 1.804/1.817 | 1.812/1.807 | 1.809/1.816 |
| Acetabular Reamer Cup of the U.S. Pat. No. 4,811,632 | | | | |
| Diameter | 1.829 | 1.794 | 1.818 | 1.804 |
| Spherocity | 1.829/1.796 | 1.794/1.813 | 1.818/1.796 | 1.804/1.831 |

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto.

What is claimed is:

1. An acetabular reamer cup comprising a cutting bowl having a plurality of singly curved cutting edges, said cutting bowl having a plurality of slots preceding said cutting edges, said cutting bowl defining an axis of rotation, said cutting edges being spirally arranged about said axis, and a bottom joined to said cutting bowl, said bottom having a tool driver opening coaxial with said cutting bowl.

2. The acetabular reamer cup of claim 1 wherein said cutting edges are curved so as to be substantially parallel to said cutting bowl and are disposed to cut upon rotation of said acetabular reamer.

3. An acetabular reamer cup comprising a cutting bowl having a plurality of singly curved cutting edges, said cutting bowl having a plurality of slots preceeding said cutting edges, said cutting bowl defining an axis of rotation, one of said cutting edges intersecting said axis of rotation and lying in a plane extending radial to said axis of rotation, the remaining of said cutting edges each extending at an angle between about 17° and about 20° to a plane extending radial to said axis of rotation, and a bottom joined to said cutting bowl, said bottom having a tool driver opening coaxial with said cutting bowl.

4. The acetabular reamer cup of claim 1 wherein one of said cutting edges intersects said axis of rotation and lies in a plane extending radial to said axis of rotation and the remaining said cutting edges each extend at an angle of about 17 degrees to a plane extending radial to said axis of rotation.

5. The acetabular reamer cup of claim 1 wherein said plurality of cutting edges further comprises between four and nine cutting edges.

6. The acetabular reamer cup of claim 1 wherein said cutting edges, upon rotation of said cutting bowl about said axis of rotation, each sweep an area overlapped by other of said cutting edges a total of about one and one-half times.

7. The acetabular reamer cup of claim 1 wherein said cutting bowl is of 19 gauge, 410 stainless steel.

8. The acetabular reamer cup of claim 4 wherein the end of said cutting edges most adjacent said bottom is the leading edge of said cutting edges.

9. The acetabular reamer cup of claim 3 wherein the end of said cutting edges most adjacent said bottom is the trailing edge of said cutting edges.

10. An acetabular reamer cup comprising a cutting bowl having a surface of revolution and an axis of rotation, said cutting bowl having a plurality of cutters extending outwardly from said surface of revolution, said cutters each having a singly curved cutting edge disposed in constant spaced relation to said surface of revolution, said cutting edges being spirally arranged about said axis, said cutting bowl having a plurality of slots preceeding said cutting edges, and a bottom joined to said cutting bowl, said bottom having a tool driver opening coaxial of said cutting bowl.

11. The acetabular reamer cup of claim 10 wherein said slots each have two pair of opposed margins, said margins each being substantially singly curved.

12. The acetabular reamer cup of claim 11 wherein said slots each have a pair of short margins and a pair of long margins, said long margins each having a length about equal to five times the length of said short margins.

13. The acetabular reamer cup of claim 10 wherein said cutting edges are curved so as to be substantially parallel to said cutting bowl and are disposed to cut upon rotation of said acetabular reamer.

14. The acetabular reamer cup of claim 10 wherein one of said cutting edges intersects said axis of rotation and lies in a plane extending radial to said axis of rotation and the remaining said cutting edges each extend at an angle between about 17 degrees and about 20 degrees to a plane extending radial to said axis of rotation.

15. The acetabular reamer cup of claim 10 wherein one of said cutting edges intersects said axis of rotation and lies in a plane extending radial to said axis of rotation and the remaining said cutting edges each extend at an angle of about 17 degrees to a plane extending radial to said axis of rotation.

16. The acetabular reamer cup of claim 10 wherein said plurality of cutting edges further comprises between four and nine cutting edges.

17. The acetabular reamer cup of claim 10 wherein said cutting edges, upon rotation of said cutting bowl about said axis of rotation, each sweep an area overlapped by other of said cutting edges a total of about one and one-half times.

18. The acetabular reamer cup of claim 10 wherein said cutting bowl is of 19 gauge, 410 stainless steel.

19. The acetabular reamer cup of claim 10 wherein the end of said cutting edges most adjacent said bottom is the leading edge of said cutting edges.

20. The acetabular reamer cup of claim 10 wherein the end of said cutting edges most adjacent said bottom is the trailing edge of said cutting edges.

* * * * *